United States Patent [19]

Dittrich et al.

[11] Patent Number: 6,077,249

[45] Date of Patent: Jun. 20, 2000

[54] TUBULAR SHAFT INSTRUMENT

[75] Inventors: Horst Dittrich, Immendingen; Uwe Bacher, Tuttlingen, both of Germany

[73] Assignee: Karl Storz GmbH & Co. KG, Germany

[21] Appl. No.: 09/200,117

[22] Filed: Nov. 25, 1998

Related U.S. Application Data

[63] Continuation of application No. PCT/EP98/01389, Mar. 11, 1998.

[51] Int. Cl.[7] .................................................. A61M 5/178
[52] U.S. Cl. ......................... 604/169; 604/256; 137/522; 251/83; 251/149.2
[58] Field of Search ..................................... 604/264, 246, 604/93, 164, 167, 169, 256, 248; 600/114; 606/108; 137/522, 523; 251/82–83, 149.2

[56] References Cited

U.S. PATENT DOCUMENTS

| | | | |
|---|---|---|---|
| 5,397,314 | 3/1995 | Farley et al. | 604/256 |
| 5,399,167 | 3/1995 | Deniega | 604/164 |
| 5,591,192 | 1/1997 | Privitera et al. | 604/164 |

*Primary Examiner*—Corrine McDermott
*Assistant Examiner*—Jeremy Thissell
*Attorney, Agent, or Firm*—St. Onge Steward Johnson & Reens LLC

[57] ABSTRACT

A tubular shaft instrument, in particular a trocar, has an instrument channel which can be closed off by a flap valve. An actuation element serves to open the flap valve against the force of a closing spring. It is proposed that the actuation element be configured as an element which at least partly surrounds the instrument channel and can rotate about the instrument channel axis, and which is equipped with a circumferential cam bevel, rising in the direction of the instrument channel axis, on which a control section of the flap valve rests, so that a rotation of the rotatable element effects opening or closing of the flap valve.

9 Claims, 5 Drawing Sheets

TUBULAR SHAFT INSTRUMENT

This application is a continuation of pending international application PCT/EP98/01389 filed on Mar. 11, 1998, which designated the United States.

BACKGROUND OF THE INVENTION

The present invention relates to a tubular shaft instrument, in particular a trocar, having an instrument channel which can be closed off by a flap valve, and having an actuation element for opening the flap valve against the force of a closing spring.

A tubular shaft instrument of this kind in the form of a trocar is known from DE 39 23 243 C2.

The flap valve contains a flap which, in the closed state, extends perpendicular to the instrument channel. The flap is pivotable about a pivot axis laid alongside the instrument channel, and is pushed in the closing direction by the force of a closing spring.

The actuation element for opening the flap valve consists of an annular disk which surrounds the instrument channel and is axially displaceable in the direction of the instrument channel axis. The disk is joined to the flap of the flap valve via a plunger extending along the instrument channel axis. The plunger is arranged alongside the instrument channel, and encounters the closed flap valve in a region adjacent to the pivot axis or the hinge axis on which the flap valve is articulated. To open the flap valve, the actuation element is displaced axially so that the plunger is also axially displaced and pushes the flap valve up. The instrument channel is now open, so that an instrument, for example a trocar mandrel or an endoscope, can be slid through the trocar. A spring presses the released actuation element back into its initial position, and the flap valve then pivots in the closing direction until it encounters the inserted instrument. Depending on the configuration of the exterior of the instrument, the latter can simply be withdrawn, after which the flap valve is pressed back into the closed position because of the closing spring and closes off the instrument channel. The result is that, for example when instruments are being changed, no gases or fluids can emerge through the instrument channel from the body into which the trocar has been introduced. If the flap valve lying against the instrument should first be moved away from the latter in order to withdraw the instrument, the actuation element is once again axially displaced and the flap valve is again pivoted via the plunger into its maximum open position.

This design requires a relatively large installation space alongside the actual instrument channel, and in the case of small trocars (for example pediatric trocars) leads to unnecessarily protruding sizes. With many tubular shaft instruments it is moreover desirable to require as little radial width as possible in terms of the usable open inside diameter of the instrument channel.

DE 70 04 051 U1 discloses a trocar sleeve whose instrument channel can also be closed off via a flap valve.

A cylinder mounted with limited displaceability, which rests with its one annular end surface on the closed flap, is provided in order to open the flap. A slotted plastic spring washer is placed in the interior of the cylinder.

If a trocar mandrel is now placed into the trocar sleeve, its tip encounters the slotted spring washer, penetrates partially through it, and thereby expands it slightly until sufficient frictional engagement has been created so that further advancing of the trocar mandrel distally displaces the displaceably mounted cylinder which carries the slotted spring washer. The distal end of the cylinder thereby pushes up the flap of the flap valve. Because the cylinder can be slid forward over only a limited distance, it strikes against a stop, so that further advancing of the trocar mandrel causes the slotted spring washer to be opened sufficiently wide that the trocar mandrel can be displaced distally farther into the instrument channel. Upon withdrawal, the trocar mandrel pulls the cylinder back again until it strikes against a stop. As a result, the spring-loaded flap can swing in again and close off the instrument channel.

This design requires instruments matched exactly to the cylinder, in order to ensure the frictional engagement necessary for the movement sequence. If the frictional engagement between instrument and slotted spring washer is insufficient, the instrument can pass through the cylinder without displacing it and thus without causing the flap valve to open, which instead must be done by the inserted instrument; in the case of a trocar mandrel, which has a very sharp tip, this can lead to damage or jamming. If the instrument is too large as a result of production tolerances, jamming takes place between the instrument and the cylinder, thus interfering with the movement sequence.

It is an object of the present invention to develop a tubular shaft instrument of the kind cited initially in such a way that the opening and closing movements of the flap valve can be controlled in an easily handled manner using means of simple design which require little space.

SUMMARY OF THE INVENTION

According to the present invention, the object is achieved in that the actuation element is configured as an element which at least partly surrounds the instrument channel and can rotate about the instrument channel axis, and which is equipped with a circumferential cam bevel, rising in a direction parallel to the instrument channel axis, on which a control section of the flap valve rests, so that a rotation of the rotatable element effects opening or closing of the flap valve.

The advantage of using an element rotatable about the instrument channel axis on the one side and having a cam bevel on the other side is that there are no components (such as, for the example, the plunger mentioned initially) present at a great distance from the instrument channel, but rather that the elements necessary for controlling the flap valve are arranged around the instrument channel.

The rotary movement of the element for controlling the opening or closing position of the flap valve, rather than an axially directed movement, has the advantage that no forces are exerted on the instrument which might displace the tubular shaft instrument in the direction of the interior of the body. Especially in minimally invasive surgery, several different instruments are inserted in the course of an operation into a trocar, which in the meantime remains inside the patient's body. The rotary movement has no effect on the insertion depth of the trocar.

The provision of a cam bevel which, viewed in the direction of the instrument channel axis, rises toward it, and on which a control section of the flap valve rests, now makes it possible to convert the rotary movement of the rotatable element into an opening or closing pivoting movement of the flap of the flap valve.

If the cam bevel rises, for example, when viewed from distal to proximal, and if the flap is to be pivoted in the distal direction out of a closed position in which it extends perpendicular to the longitudinal direction of the instrument channel, the control section of the flap valve is in contact with the highest (most proximal) end of the cam bevel. Rotating the rotatable element causes the control section and thus the flap valve to pivot downward (in the distal direction), and thus to open. Advantageously, the movement takes place until the flap valve has just pivoted out of the instrument channel, so that the full width of the latter is available for the instrument to be inserted. In this position, the control section is in contact with the lowest (distal) end of the cam bevel.

When the rotatable element is rotated in the opposite direction, the control section can run along the cam bevel from bottom (distal) to top (proximal), pivoting the flap inward and closing off the instrument channel.

If the flap is to be pivoted in the proximal direction, the slope of the cam bevels is reversed.

This closing movement is assisted by the force of the closing spring which acts on the flap in the closing direction. The opening movement is done against the force of the closing spring.

The rotatable element which at least partially surrounds the instrument channel can easily be gripped and rotated from the outside with one hand. For stability reasons, the rotatable element will in most cases completely surround the instrument channel, but it is also sufficient if the instrument channel is surrounded only partially, e.g. over half or three-quarters of a circle.

In a further embodiment of the invention, the rotatable element has two cam bevels opposite one another and running in the same direction, so that a rotation of the rotatable element in one direction or the opposite direction causes the same movement of the flap valve in each case.

This feature has the considerable advantage that regardless of the rotation direction, the flap valve can be opened by way of the two cam bevels which run in the same direction and are located approximately diametrically opposite one another. The control section of the flap valve is configured in that it is in contact with both cam bevels. The flap is opened each time, regardless of whether the rotatable element is turned clockwise or counter-clockwise. This has the considerable advantage, in terms of easy handling, that the user does not need to remember a specific rotation direction for opening the flap valve, but rather that this can be accomplished in both possible rotation directions.

In a further embodiment of the invention, the rotatable element is configured as a sleeve whose end facing the flap valve is cut off obliquely, the cut edges constituting the cam bevels.

This feature has the advantage, in terms of design and production engineering, that simple means are used to create a radially narrow rotatable element whose end is cut off obliquely, the cam bevels then being constituted as a result.

In a further embodiment of the invention, the end of the rotatable element is cut off obliquely over approximately half a circumference.

The advantage of this feature is that a rotation of the element through 90 degrees in one direction or in the opposite direction effects a complete opening of the valve flap in each case. At the same time it is possible, in the cut-off section, for the pivoted-in (i.e. closed) valve flap to pivot into the interior of the instrument in order to close off the instrument channel. In the closed-off state, the flap has thus entered via the cut-off region into the end section of the rotatable element or the sleeve. In this state, the flap is then protected by the regions that were not cut off and which surround half a circumference of the flaps. There is no risk of damaging the closed valve flap during disassembly or assembly of the instrument.

In a further embodiment of the invention, the cut angle extends at approximately 45 degrees to the instrument channel axis.

This geometry allows favorable force transfer from the rotating element to the flap valve with no need for large force peaks at the beginning or end, so that a uniform and harmonious opening movement is ensured, which is very convenient in terms of handling.

In a further embodiment of the invention, the rotatable element is equipped with at least one radially projecting grip element.

The advantage of this feature is that a lever effect can be attained by way of the radially projecting grip element, so that a relatively small force is required to open the flap. It is particularly advantageous in combination with pivotability in both directions, i.e. it is necessary simply to grasp the radially projecting grip element with a finger, or place a finger on it, and then pivot it in one direction or the other.

In a further embodiment of the invention, two diametrically opposite radially projecting grip elements are provided.

The advantage of this feature is that several favorable placement positions for the fingers of one hand are provided, so that the rotatable element can be rotated with little energy expenditure so as thereby to open or close the flap valve.

In a further embodiment of the invention, the rotatable element is rotatable against the force of a torsion spring which forces the rotatable element into a rotary position in which the flap valve is closed.

This feature has the advantage that if, for example, the rotary element is rotated so that the flap is thereby opened, the rotatable element does not need to be moved further, but rather it is moved by the torsion spring itself back into its initial position. For example, when an instrument is withdrawn, the forces of the springs—namely the spring which pushes the flap in the closing direction and the torsion spring—cause the control section to move automatically into the closed position along the cam bevel or bevels, the rotatable element correspondingly being automatically rotated. This feature is also particularly convenient in terms of handling, and moreover ensures that when an instrument has been withdrawn, the instrument channel is closed off by the flap valve, so that no gases or fluids can undesirably pass through the instrument channel.

In a further embodiment of the invention, the torsion spring is arranged in an annular space between the outer side of the rotatable element and an inner side of a housing enclosing the element.

This feature also results in a slender design, since the torsion spring is now also arranged in an annular space which does not require radial protrusions.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described and explained in more detail below with reference to a selected exemplifying embodiment, in conjunction with the appended drawings in which.

DETAILED DESCRIPTION OF A PREFERRED EMBODIMENT

A tubular shaft instrument depicted in the Figs. is designated in its entirety with the reference number 10.

In the exemplifying embodiment depicted, tubular shaft instrument 10 is configured as a trocar 12.

Figure 1:
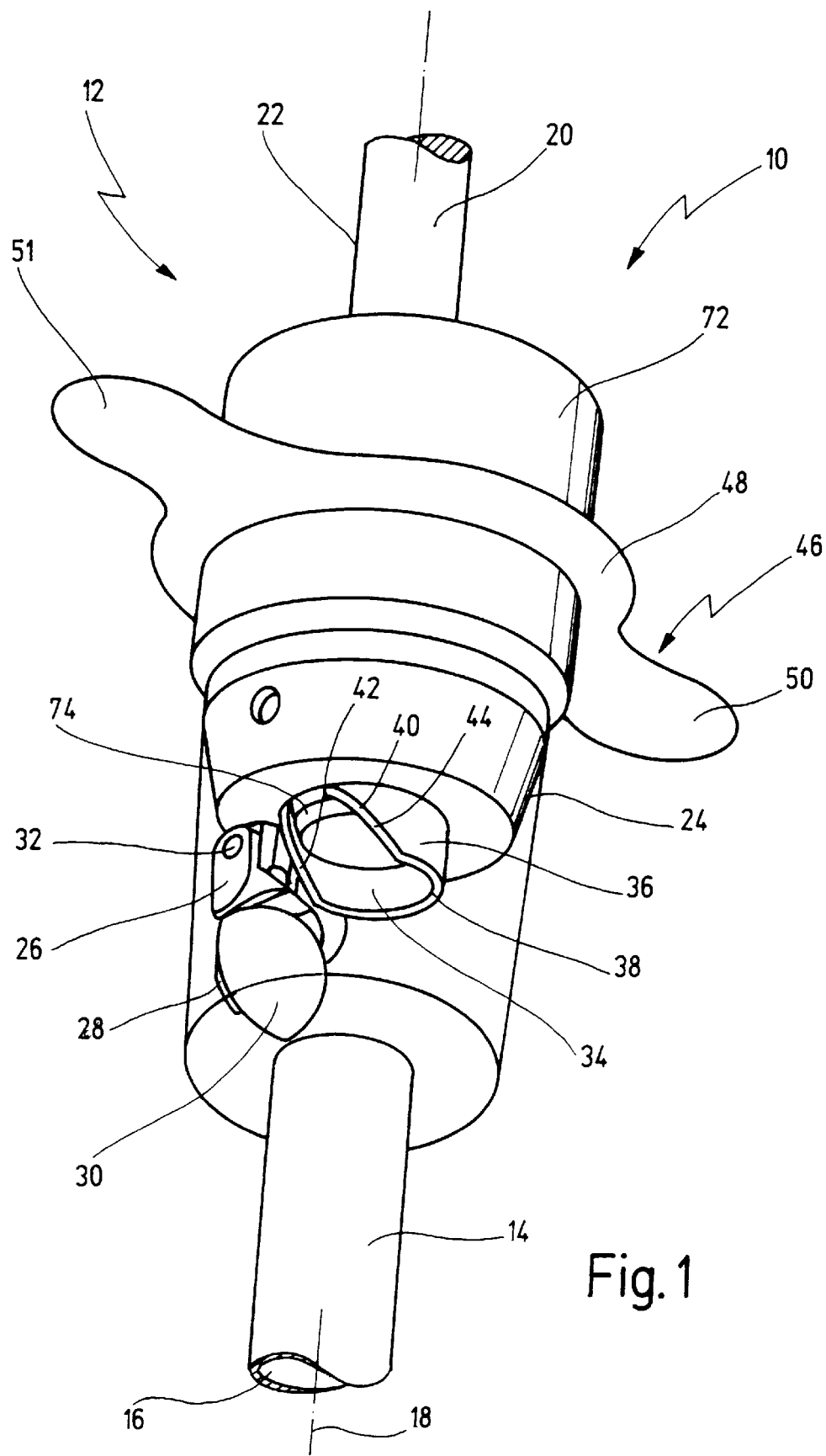
FIG. 1 shows in schematic fashion a perspective view of a trocar, viewed from distal to proximal, with the flap valve open.

Trocar 12 shown in FIG. 1 has a trocar sleeve 14 which surrounds an instrument channel 16. A central longitudinal axis of the instrument channel 16 is designated as instrument channel axis 18. An instrument 20, for example a trocar mandrel 22, is to be introduced from the proximal end into sleeve 14 of trocar 12.

A housing 24, in the interior of which a flap valve 26 is provided, is provided at the proximal end of trocar sleeve 14.

Flap valve 26 has a pivotable flap 28 which carries a semi-spherical seal 30.

Flap 28 is articulated, pivotably about a pivot pin 32, on housing 24.

Pivot pin 32 extends laterally next to instrument channel 16 and perpendicular to instrument channel axis 18.

A spring 33 (see FIG. 3) acts on flap 28, specifically so as to move the latter into its closed position.

In the depiction of FIG. 1, flap valve 26 is completely open, and instrument channel 16 is thus uncovered so that trocar mandrel 22, for example, can be slid through trocar 12.

Figure 2:
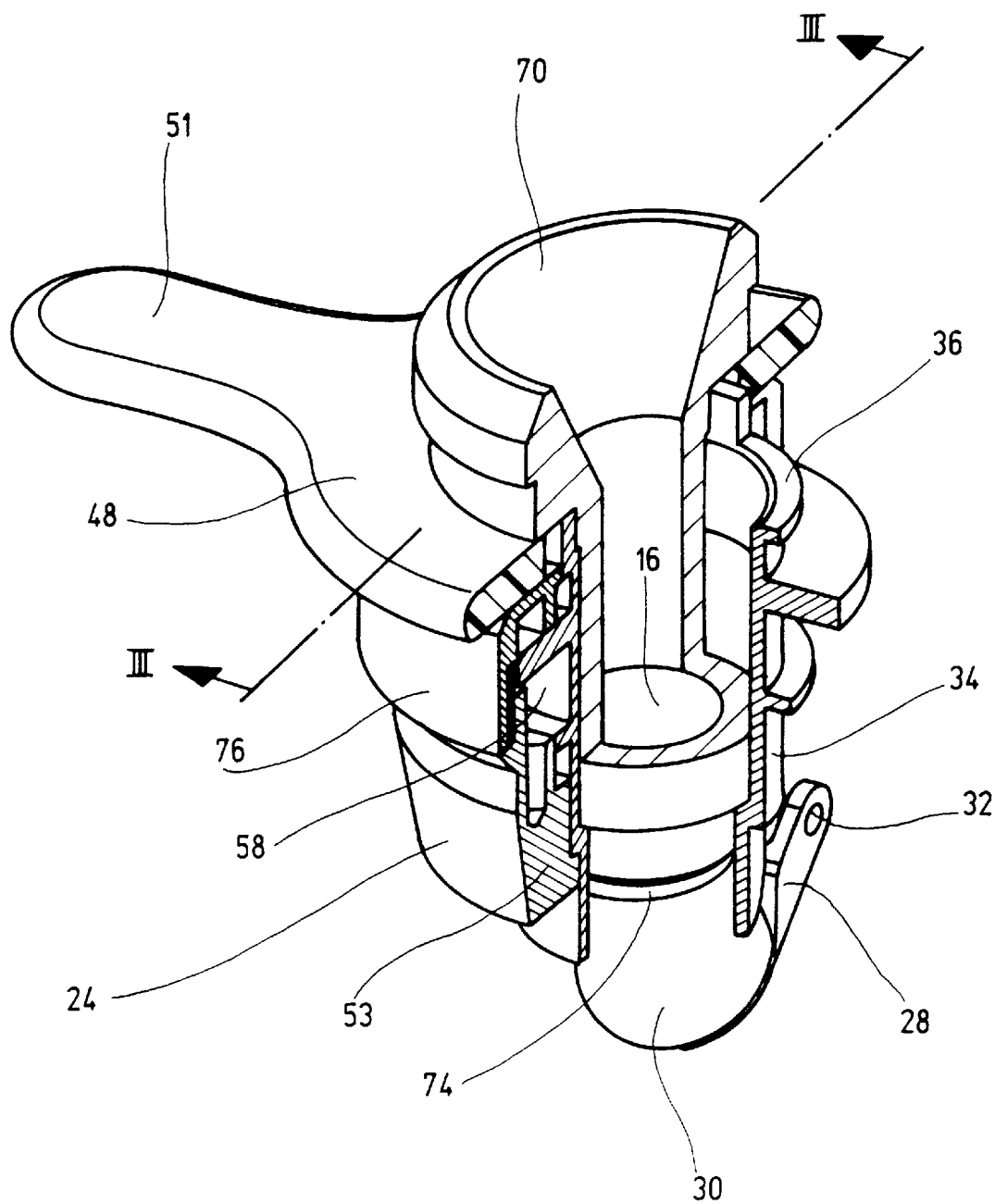
FIG. 2 shows a partially cutaway perspective view of the trocar of FIG. 1, with the flap valve in the almost-closed state.
Figure 3:
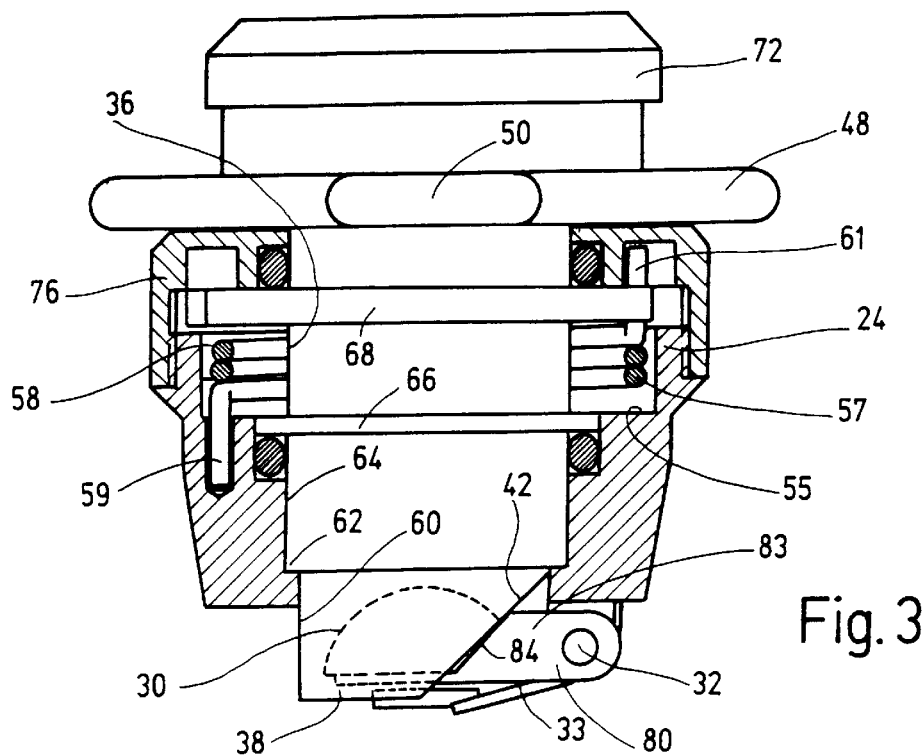
FIG. 3 shows a section along line III—III in FIG. 2, the flap valve being shown in the completely closed state.

Received in housing 24 is a rotatable element 34 in form of a sleeve 36, as is better evident in particular from the sectioned depictions of FIGS. 2 and 3, sleeve 36 being merely sketched in the depictions of FIG. 3.

Sleeve 36 is received in housing 24 in such a way that it surrounds instrument channel 16.

As shown in FIG. 1, a lower end 38 of sleeve 36 projects in the distal direction from housing 24. Directly next to this, flap 28 is articulated via pivot pin 32.

Lower end 38 of sleeve 36 is equipped with an obliquely extending cut edge 40, i.e. except for approximately half the circumference, end 38 is cut off obliquely at an angle of approximately 45 degrees.

The result is to create two cam bevels 42 and 44, arranged approximately diametrically opposite one another and running in the same direction, which in the depiction of FIG. 1 each rise in the proximal direction from lower end 38.

At the end opposite end 38, sleeve 36 is joined via an attachment piece 76 to a grip 46, as shown in the sectioned depiction of FIG. 2. Grip 46 has a ring 48, surrounding sleeve 36, from which two diametrically opposite grip elements 50, 51 project radially.

A recess 55 is provided in an inner wall 53 of housing 24, as is visible in particular in the sectioned depiction of FIG. 3. This creates, between the outer side of sleeve 36 and the inner side of housing 24, an annular space 58 in which a torsion spring 57 is received.

Figure 4:
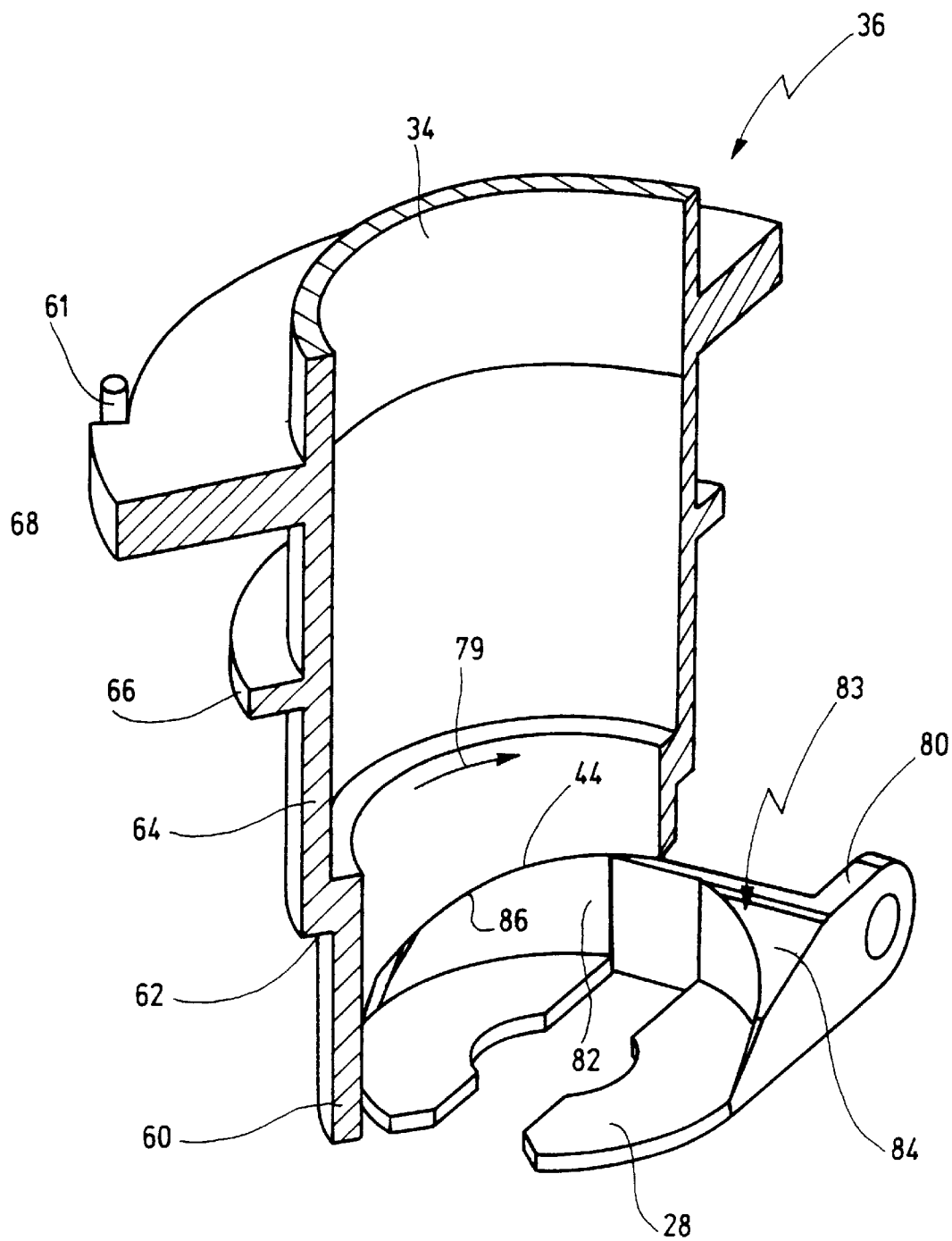
FIG. 4 shows a greatly enlarged schematic representation of the coaction of an actuation element and the flap valve, with the flap valve still in the closed state.

Torsion spring 57 is wound in helical fashion around the outer side of sleeve 36; one end 59 is anchored in wall 53 of housing 24, and the other end 61 is in engagement with a flange 68 of sleeve 36 (see also FIG. 4).

As shown in FIGS. 3 and 4, sleeve 36 has a lower end section 60 which transitions, via a shoulder 62, into a center section 64 of somewhat greater diameter.

Projecting from the outer side of section 64 in axially spaced fashion are two annular flanges 66 and 68 between which torsion spring 57 is received, as shown in FIG. 3.

As is evident from the cutaway depiction of FIG. 2, an insert 70 is pushed from above into sleeve 36 and peripherally delimits the actual instrument channel 16. One lower end of insert 70 represents a valve seat 74 (see FIGS. 1 and 2) for semispherical seal 30 of flap valve 26. In the completely assembled state, a cap 72 is also placed onto insert 70.

When flap valve 26 is in the closed state, as is visible in the sectioned depiction of FIG. 3, flap 28 is pivoted into instrument channel 16 and rests sealingly against the aforementioned valve seat 74. Flap 28 is thereby located in the interior of the lower end section 60 of sleeve 36. The two diametrically opposite cam bevels 42 and 44 are thereby in contact with a control section 83 of flap 28 of flap valve 26.

Figure 5:
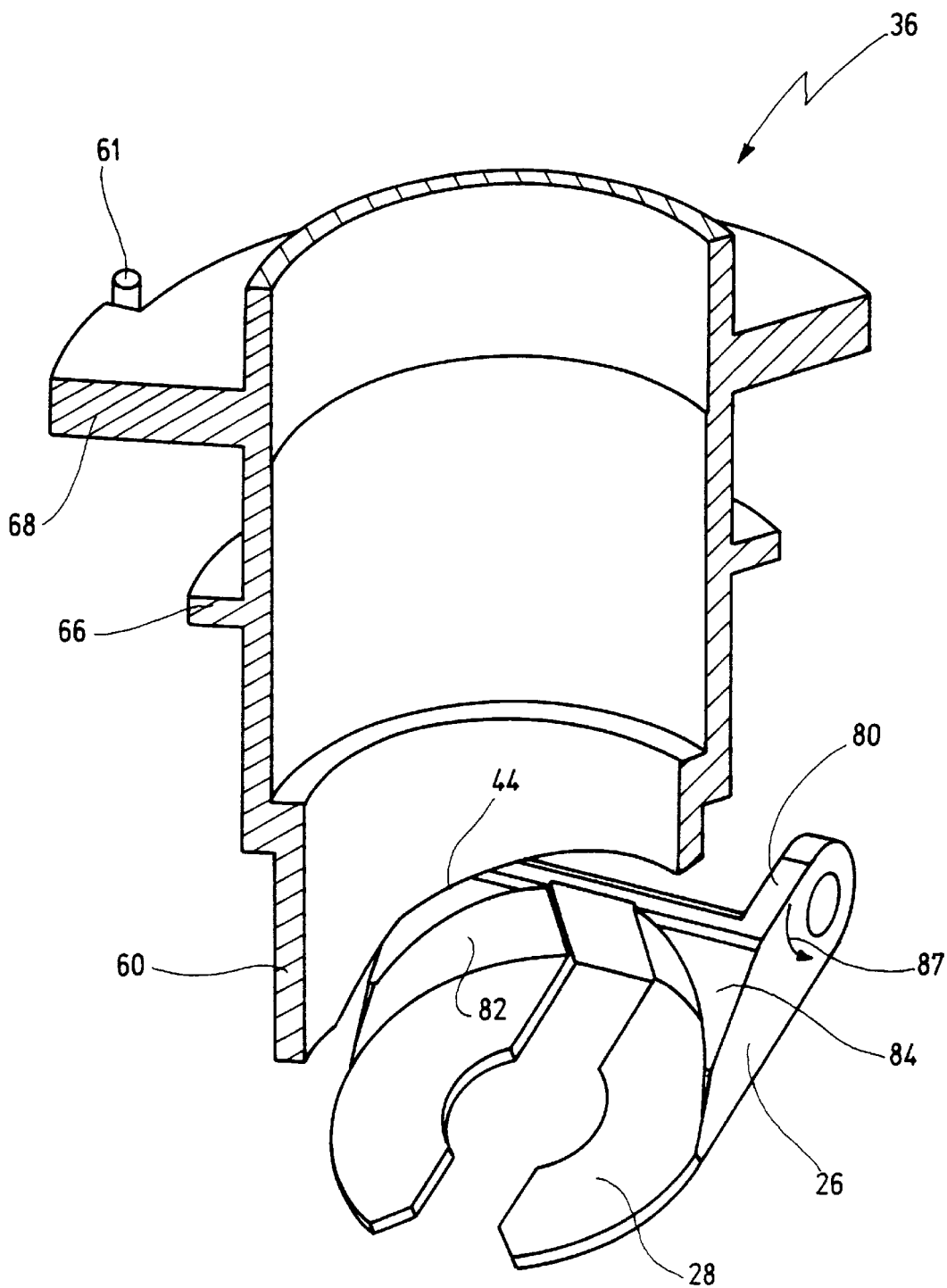
FIG. 5 shows a representation corresponding to that of FIG. 4, with the flap valve in a partially-open state.

As shown in the enlarged depiction of FIG. 4, flap 28 comprises a planar base part into which semispherical seal 30 is pressed; for the sake of clarity, this semispherical seal 30 has been omitted from the depictions of FIGS. 4 and 5. Two brackets 80 and 82 project in fork fashion, approximately tangentially, from the base part (not designated here in more detail), and are equipped with corresponding aligning openings into which pivot pin 32 is inserted. At the same time, pivot pin 32 is inserted through corresponding aligning openings of assembly brackets on the underside of housing 24, thus pivotably attaching flap 28.

The upper (in the depiction of FIGS. 4 and 5) edges of brackets 80 and 82 transition via bevels 84 and 86 into the base part of flap 28. This region, i.e. the transition region of the upper edges of brackets 80 and 82 and bevels 84 and 86, constitute control section 83 which is in contact with cam bevels 42 and 44.

In the closed state, as shown in FIG. 3, bracket 80 is in contact, approximately in the transition region between its upper edge and bevel 34, with cam bevel 42. The same is true for bracket 82 and cam bevel 44. When sleeve 36 is then rotated via one of grip elements 50 or 51 as indicated in FIG. 3a by an arrow 77, cam bevel 42 pushes flap 28 away downward, and the transition region, configured as a control cam, between the upper edge of bracket 38 and bevel 84 runs downward along cam bevel 24.

Figure 3A:
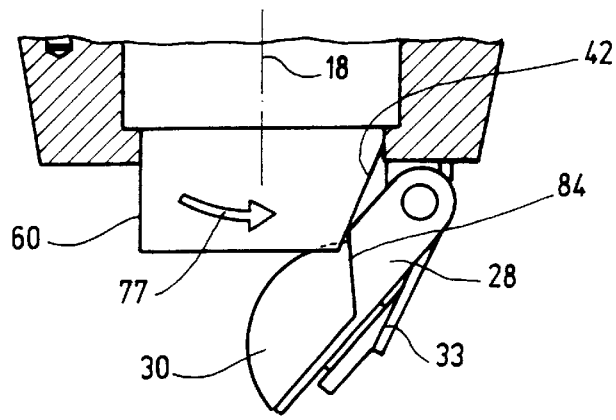
FIG. 3a shows a lower portion of the representation of FIG. 3, with the flap valve in a partially-open state.
Figure 3B:
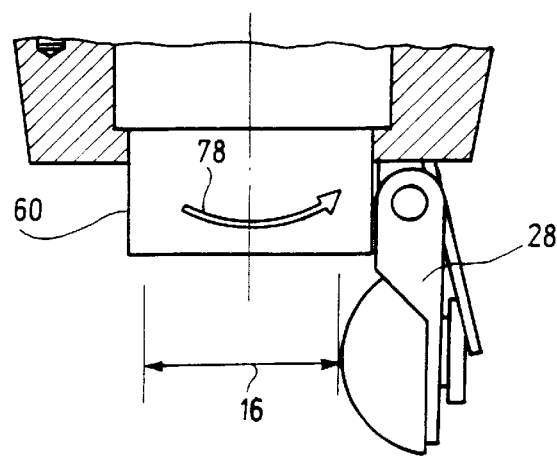
FIG. 3b shows a representation corresponding to that of FIG. 3a, with the flap valve completely open.

A further rotation, as indicated in the transition from FIG. 3a to 3b by an arrow 78, then results in complete opening of flap 28, i.e. the latter is pivoted completely out of instrument channel 16.

This movement sequence is depicted once again in the enlarged partial depictions of FIGS. 4 and 5, the reverse rotation direction now being depicted.

In other words, as shown in FIG. 4, sleeve 36 is moved in the direction of an arrow 79, i.e. exactly opposite to the direction of arrow 77 of FIG. 3a. In this case, cam bevel 44 then comes into engagement with the corresponding control section of bracket 82, and opens or pivots flap 28 in the same direction as in the case of the sequence of FIGS. 3, 3*a*, and 3*b*.

Flap 28 is thus opened in both rotation directions of sleeve 36.

Because sleeve 36 is in engagement with one end 61 of torsion spring 57, as indicated in FIG. 4, rotation of sleeve 36 causes tensioning of torsion spring 57 so that the latter tends to rotate sleeve 36 back into the initial position (FIGS. 3 and 4).

For example, if grip elements 50, 51 were released from the position depicted in FIG. 3*b*, torsion spring 57 would rotate sleeve 36 back, and because of the force of spring 33, flap valve 26 would at the same time also be closed again.

We claim:

1. A tubular shaft instrument, having
    a tubular shaft surrounding an instrument channel
    a flap valve for closing and opening said instrument channel,
    an actuation element for actuating said flap valve between a closing and an opening position, and
    a closing spring acting on said flap valve in order to force said flap valve into its closing position,
wherein
    said actuation element is configured as an element which at least partly surrounds said instrument channel and can rotate about a central instrument channel axis, and which element is equipped with a circumferential cam bevel rising in a direction parallel to said instrument channel axis, on which a control section of said flap valve rests, a rotation of said rotatable element effects opening or closing of said flap valve.

2. The tubular shaft instrument of claim 1, wherein said rotatable element is provided with two cam bevels opposite one another and running in the same direction, a rotation of said rotatable element in one direction or into the opposite direction causes the same movement of said flap valve in each case.

3. The tubular shaft instrument of claim 1, wherein said rotatable element is configured as a sleeve whose one end facing said flap valve is cut off obliquely, respective resulting cut edges constitute a cam bevel.

4. The tubular shaft instrument of claim 3, wherein said end of said rotatable element is cut off obliquely over approximately half a circumference.

5. The tubular shaft instrument of claim 4, wherein a cut angle extends at approximately 45 degrees to said instrument channel axis.

6. The tubular shaft instrument of claim 1, wherein said rotatable element is equipped with at least one radially projecting grip element.

7. The tubular shaft instrument of claim 6, wherein two diametrically opposite radially projecting grip elements are provided.

8. The tubular shaft instrument of claim 1, wherein said rotatable element is rotatable against the force of a torsion spring which rotates said rotatable element into a rotary position in which said flap valve is closed.

9. The tubular shaft instrument of claim 8, wherein said torsion spring is arranged in an annular space between an outer side of said rotatable element and an inner side of a housing enclosing said rotatable element.

* * * * *